(12) United States Patent
Crawshaw et al.

(10) Patent No.: US 8,623,333 B2
(45) Date of Patent: Jan. 7, 2014

(54) COMPOSITION

(75) Inventors: Andrew Gordon Crawshaw, Weybridge (GB); Frank Lippert, Weybridge (GB)

(73) Assignee: Glaxo Group Limited, Greenford, Middlesex (GB)

( * ) Notice: Subject to any disclaimer, the term of this patent is extended or adjusted under 35 U.S.C. 154(b) by 197 days.

(21) Appl. No.: 13/121,234

(22) PCT Filed: Sep. 28, 2009

(86) PCT No.: PCT/EP2009/062499
§ 371 (c)(1),
(2), (4) Date: Mar. 28, 2011

(87) PCT Pub. No.: WO2010/037701
PCT Pub. Date: Apr. 8, 2010

(65) Prior Publication Data
US 2011/0189111 A1    Aug. 4, 2011

Related U.S. Application Data

(60) Provisional application No. 61/101,505, filed on Sep. 30, 2008.

(51) Int. Cl.
*A61K 8/21*    (2006.01)

(52) U.S. Cl.
USPC ............................................................. 424/52

(58) Field of Classification Search
USPC ............................................................. 424/52
See application file for complete search history.

(56) References Cited

U.S. PATENT DOCUMENTS

2007/0122358 A1    5/2007    Wang et al.

FOREIGN PATENT DOCUMENTS

| EP | 0 691 124 A1 | | 1/1996 |
|---|---|---|---|
| FR | 2 755 010 A1 | | 4/1998 |
| JP | 2003 089627 A | | 3/2003 |
| WO | WO2008/068323 | * | 6/2008 |
| WO | WO2008/068323 A1 | | 6/2008 |

* cited by examiner

*Primary Examiner* — Rei-tsang Shiao
(74) *Attorney, Agent, or Firm* — Nora L. Stein; Theodore R. Furman

(57) ABSTRACT

A dentifrice composition comprising a source of fluoride ions and from 0.01-1.5% w/w of a xanthan gum, from 0.01-1.5% w/w of a polyacrylic acid, from 0.01-2.0% w/w of a carageenan gum and a thickening silica and wherein the composition has a pH of between 5.5 and 6.5.

12 Claims, 3 Drawing Sheets

COMPOSITION

This application is a 371 of International Application No. PCT/EP2009/062499, filed 28 Sep. 2009, which claims priority from U.S. Provisional Application No. 61/101,505, filed 30 Sep. 2008, which is incorporated herein in its entirety.

FIELD OF THE INVENTION

This invention relates to dentifrice compositions comprising a source of fluoride ions for strengthening and protecting the enamel of natural teeth, thereby providing protection against acidic challenges. Such compositions are of use in combating (ie helping to prevent, inhibit and/or treat) dental caries. Such compositions are also of use in combating dental erosion and/or tooth wear. The compositions additionally comprise a thickening system useful for enhancing the rheology of the compositions.

BACKGROUND OF THE INVENTION

Tooth mineral is composed predominantly of calcium hydroxyapatite, $Ca_{10}(PO_4)_6(OH)_2$, which may be partially substituted with anions such as carbonate or fluoride, and cations such as zinc or magnesium. Tooth mineral may also contain non-apatitic mineral phases such as octacalcium phosphate and calcium carbonate.

Tooth loss may occur as a result of dental caries, which is a multifactorial disease where bacterial acids such as lactic acid produce sub-surface demineralisation that does not fully remineralise, resulting in progressive tissue loss and eventually cavity formation. The presence of a plaque biofilm is a prerequisite for dental caries, and acidogenic bacteria such as *Streptococcus mutans* may become pathogenic when levels of easily fermentable carbohydrate, such as sucrose, are elevated for extended periods of time.

Even in the absence of disease, loss of dental hard tissues can occur as a result of acid erosion and/or physical tooth wear; these processes are believed to act synergistically. Exposure of the dental hard tissues to acid causes demineralisation, resulting in surface softening and a decrease in mineral density. Under normal physiological conditions, demineralised tissues self-repair through the remineralising effects of saliva. Saliva is supersaturated with respect to calcium and phosphate, and in healthy individuals saliva secretion serves to wash out the acid challenge, and raises the pH so as to alter the equilibrium in favour of mineral deposition.

Dental erosion (i.e. acid erosion or acid wear) is a surface phenomenon that involves demineralisation, and ultimately complete dissolution of the tooth surface by acids that are not of bacterial origin. Most commonly the acid will be of dietary origin, such as citric acid from fruit or carbonated drinks, phosphoric acid from cola drinks and acetic acid such as from vinaigrette. Dental erosion may also be caused by repeated contact with hydrochloric acid (HCl) produced in the stomach, which may enter the oral cavity through an involuntary response such as gastroesophageal reflux, or through an induced response as may be encountered in sufferers of bulimia.

Tooth wear (ie physical tooth wear) is caused by attrition and/or abrasion. Attrition occurs when tooth surfaces rub against each other, a form of two-body wear. An often dramatic example is that observed in subjects with bruxism, a grinding habit where the applied forces are high, and is characterised by accelerated wear, particularly on the occlusal surfaces. Abrasion typically occurs as a result of three-body wear and the most common example is that associated with brushing with a toothpaste. In the case of fully mineralised enamel, levels of wear caused by commercially available toothpastes are minimal and of little or no clinical consequence. However, if enamel has been demineralised and softened by exposure to an erosive challenge, the enamel becomes more susceptible to tooth wear. Dentine is much softer than enamel and consequently is more susceptible to wear. Subjects with exposed dentine should avoid the use of highly abrasive toothpastes, such as those based on alumina. Again, softening of dentine by an erosive challenge will increase susceptibility of the tissue to wear.

EP-A-691124 (Sara Lee) describes oral care products comprising a copolymer of N-vinylpyrrolidone and acrylic acid, said to result in enhanced enamel fluoride uptake in the tooth enamel. On page 11 of Sara Lee the relative enamel fluoride uptake efficacy of various formulations containing different thickening agents, including a combination of xanthan gum and a carbopol is described.

French Patent No. 2755010 (Sara Lee) describes an oral care product containing fluoride comprising a combination of xanthan gum and a carboxylated vinyl polymer. Sara Lee specifically claim the use of this combination to enhance the efficacy of the fluoride. There is no specific disclosure of an oral care product containing any other thickening agents, although it is suggested that an oral care product such as a toothpaste may comprise various thickening agents including hectorite, carrageenan, gum tragacanth, starch, polyvinylpyrrolidone, various hydroxyalkyl celluloses, carboxymethylcellulose sodium and colloidal silica.

WO 08/068,323 describes a post-foaming dentifrice composition having a viscosity of at least 80,000 mPas comprising a combination of a first thickening agent which is xanthan gum, a second thickening agent which is carrageenan and/or a polyacrylic acid and a third thickening agent which is a thickening silica, together with a post-foaming agent to expand the composition to a foam. The Examples in WO 08/068,323 all show dentifrice compositions with a thickening system that comprises xanthan gum, carageenan and a thickening silica, and is incorporated by reference herein.

Contrary to the teaching in the above noted Sara Lee patent, the present applicants have found that the combination of xanthan gum and a polyacrylic acid (ie a carboxylated vinyl polymer) in an oral care product does not result in enhanced fluoride efficacy when compared with a corresponding product containing a polyacrylic acid in the absence of xanthan gum. It appears from Example 4 of the present specification that the presence of xanthan gum reduces the enhanced efficacy of oral care products containing a polyacrylic acid.

In addition the present applicants have found that oral care products containing the combination of xanthan gum, a polyacrylic acid and a thickening silica can suffer problems of poor rheology, such that the products are too runny and provide poor stand-up when dispensed onto a toothbrush.

The applicants have found that such problems can be overcome by using xanthan gum, carageenan gum, polyacrylic acid and a thickening silica as the thickening system in a dentifrice composition. This new formulation shows good stability plus excellent build and structure and therefore produces good stand-up when dispensed onto a toothbrush. The good build and structure that is produced proves particularly beneficial when preparing a striped dentifrice product.

SUMMARY OF THE INVENTION

Accordingly the present invention provides dentifrice composition comprising a source of fluoride ions, and as the thickening system a combination of from 0.01-1.5% w/w of a xanthan gum, from 0.01-1.5% w/w of a polyacrylic acid, from 0.01-2.0% w/w of a carageenan gum and a thickening silica and wherein the composition has a pH of between 5.5 and 6.5.

Additionally, compositions of the present invention show good enamel strengthening coupled with good enamel protection properties as shown in the data below. The degree of enamel strengthening may be calculated from Enamel Fluoride Uptake (EFU) data whilst enamel protection may be calculated from Enamel Solubility Reduction (ESR) data.

DETAILED DESCRIPTION OF THE INVENTION

Figure 1:
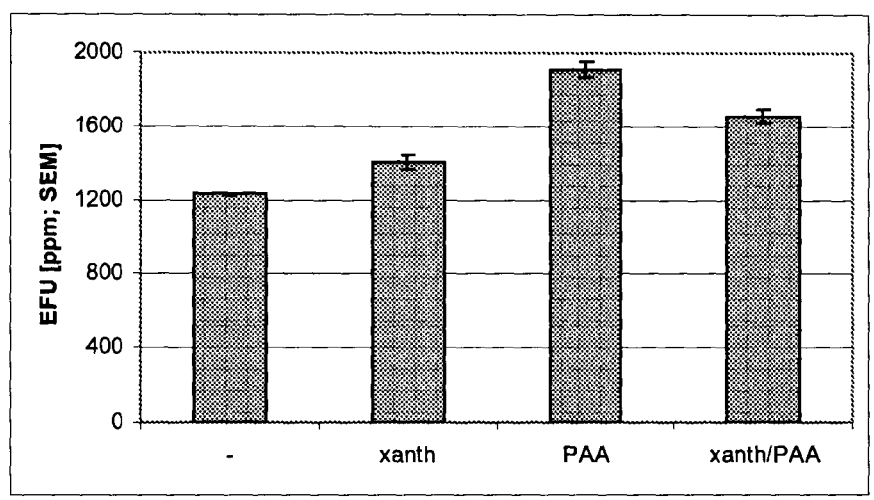
FIG. 1 depicts the results of an in vitro study conducted to determine the effect of various solutions containing xanthan gum and/or PAA at pH 6.0 on promoting fluoride uptake into incipient enamel lesions.

Suitably the xanthan gum is present in an amount from 0.1 to 1.0%, for example from 0.5 to 1.0% by weight of the total composition.

A suitable xanthan gum for use in the present invention is Keltrol F. Keltrol F is available from the company CP Kelco Biospecialities Group, USA.

Suitably the polyacrylic acid is present in an amount from 0.1 to 1.0%, for example from 0.2 to 0.6% by weight of the total composition Suitably examples of a polyacrylic acid include a carbomer, an acrylate/alkyl acrylate cross polymer or a polycarbophil. A most suitable carbomer for use in the present invention is of the Carbopol® type, available from the company B.F Goodrich, for example Carbopol® 980 or Carbopol® ETD 2020 NF. Particularly suitable is Carbopol® ETD 2020 NF.

Suitably, the carageenan is present in an amount from 0.05 to 0.5%, for example from 0.1 to 0.3% by weight of the total composition.

A suitable carageenan for use in the present invention is Genuvisco TPH-1. Genuvisco TPH-1 is available from CP Kelto Biospecialities Group, USA.

In addition to the above thickeners a thickening silica, which is a silicas that has relatively little abrasive effect compared with known abrasive silicas, is present. The thickening silica is included to further improve the rheology of the composition.

Suitable thickening silicas are known and include those marketed by Huber under the tradename Zeodent, e.g. Zeofree 153B and Zeodent 167; by Degussa AG under the trade name SIDENT®, e.g. SIDENT 225®; and by Grace-Davison Chemical Division under the trade name SYLOBLANC®, e.g. SYLOBLANC 15®.

A suitable thickening silica for use in the present invention is Zeofree 153B. For example the composition may contain up to 20% by weight of the total composition of a thickening silica, typically 5-15% by weight of the total composition.

Suitably the pH of the composition is from 5.5 to 6.5, for example from 5.5 to 6.0. Typically the composition may contain up to 0.5% by weight of the total composition of sodium hydroxide to provide a suitable pH.

Compositions of the present invention may also comprise a dental abrasive, such as a silica abrasive, or may contain no added abrasive, eg as described in WO 05/027858 (Glaxo Group Ltd).

Examples of suitable silica dental abrasives include those marketed under the following trade names Zeodent, Sident, Sorbosil or Tixosil by Huber, Degussa, Ineos and Rhodia respectively.

Suitably a silica abrasive is present in an amount up to 25% by weight of the total composition, for example from 2 to 20% by weight for example from 5 to 15% by weight of the total composition.

In addition to a source of fluoride ions, compositions of the present invention may comprise one or more active agents conventionally used in dentifrice compositions, for example, a desensitising agent, an antimicrobial agent, an anti-plaque agent; an anti-calculus agent, a whitening agent, an oral malodour agent or a mixture of at least two thereof. Such agents may be included at levels to provide the desired therapeutic effect.

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 pm of fluoride ions, preferably from 100 to 1500 ppm. A typical fluoride source is sodium fluoride, for example the composition may contain 0.1 to 0.5% by weight of sodium fluoride, eg 0.204% by weight (equating to 927 ppm of fluoride ions), 0.2542% by weight (equating to 1150 ppm of fluoride ions) or 0.315% by weight (equating to 1426 ppm of fluoride ions).

Such fluoride ions help promote the remineralisation of teeth and can increase the acid resistance of dental hard tissues for combating caries, dental erosion (ie acid wear) and/or tooth wear. The presence of the polyacrylic acid in the compositions of present invention has been found to enhance the efficacy of fluororide ions when compared with a corresponding product containing alternative thickening agents.

In order to treat dental hypersensitivity, compositions of the present invention may comprise a desensitising agent. Examples of desensitising agents include a tubule blocking agent or a nerve desensitising agent and mixtures thereof, for example as described in WO 02/15809 (Block). Examples of desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising agent such as a potassium salt is generally present between 2 to 8% by weight of the total composition, for example 5% by weight of potassium nitrate may be used.

Compositions of the present invention may comprise a whitening agent, for example selected from a polyphosphate, eg sodium tripolyphosphate (STP) and/or any additional silica abrasive present may have high cleaning properties. STP may be present in an amount from 2 to 15%, for example from 5 to 10% by weight of the total composition. Examples of high cleaning silica abrasives include those marketed as Zeodent 124, Tixosil 63, Sorbosil AC39, Sorbosil AC43 and Sorbosil AC35 and may be present in suitable amounts as hereinbefore described.

Compositions of the present invention may comprise an oral malodour agent, for example a zinc salt such as zinc oxide.

Compositions of the present invention will contain additional formulating agents such as surfactants, humectants, flavouring agents, sweetening agents, opacifying or colouring agents, preservatives and water, selected from those conventionally used in the oral hygiene composition art for such purposes.

Suitable surfactants for use in the present invention include anionic surfactants such as a sodium $C_{10-18}$alkyl sulphate, eg sodium lauryl sulphate. Sodium lauryl sulphate is generally considered to be anionic and strongly charged and is useful if high levels of foaming are desired when brushing teeth.

Alternatively zwitterionic, amphoteric and non- or low-ionic surfactants may be used in addition to or instead of an anionic surfactant.

For a dentifrice composition of the present invention comprising a desensitising agent, such as a potassium salt, typical classes of surfactants include amphoteric or mildly ionic surfactants, or mixtures thereof, these being less ionic and less strongly charged than sodium lauryl sulphate. Suitably compositions of the present invention comprising a potassium salt do not contain an anionic surfactant such as a $C_{1-18}$ alkyl sulphate, eg sodium lauryl sulphate, which, whilst it has good detergent and cleaning properties, can cause the formation of an insoluble potassium lauryl sulphate precipitate.

Examples of amphoteric surfactants include, long chain alkyl betaines, such as the product marketed under the tradename 'Empigen BB' by Albright & Wilson, long chain alkyl amidoalkyl betaines, such as cocamidopropylbetaine, or low ionic surfactants such as sodium methyl cocoyl taurate, which is marketed under the trade name Adinol CT by Croda, or a mixture of at least two thereof.

Suitably, the surfactant is present in the range 0.1 to 15%, for example from 0.5 to 10% or from 1.0 to 5% by weight of the total composition Suitable humectants for use in compositions of the invention include glycerin, xylitol, sorbitol, propylene glycol or polyethylene glycol, or mixtures of at least two thereof; which humectant may be present in the range from 10 to 80%, for example from 20 to 70% or from 30 to 60% by weight of the total composition.

The compositions according to the present invention may be prepared by admixing the ingredients in the appropriate relative amounts in any order that is convenient and if necessary adjusting the pH to give a final desired value.

The pH is measured when the composition is slurried with water in a 1:3 weight ratio of the composition to water.

The composition of the present invention is suitable for containing in and dispensing from a laminate tube or a pump as conventionally used in the art.

A typical process for making the composition of this invention involves admixing the ingredients, suitably under a vacuum, until a homogeneous mixture is obtained, and adjusting the pH if necessary.

The invention will now be described by way of the following non-limiting examples.

TABLE 1

| Raw Material | Dentifrice Composition | | | | | |
| --- | --- | --- | --- | --- | --- | --- |
| | Ex 1 % w/w | Ex 2 % w/w | Ex 3 % w/w | Ex A % w/w | Ex B % w/w | Ex C % w/w |
| Sorbitol, Liquid (Non-Crystallising) | 28.00 | 28.00 | 28.00 | 28.00 | 28.00 | 28.00 |
| Glycerol | 4.00 | 4.00 | 4.00 | 4.00 | 4.00 | 4.00 |
| Polyethylene Glycol 300 (PEG 6) | 3.00 | 3.00 | 3.00 | 3.00 | 3.00 | 3.00 |
| Silica, Dental Type (Zeodent 113) | 14.00 | 14.00 | 14.00 | 14.00 | 14.00 | 14.00 |
| Silica, Dental Type (Zeofree 153B) | 9.00 | 9.00 | 9.00 | 9.00 | 9.00 | 9.00 |
| Sodium Lauryl Sulphate | 1.50 | 1.50 | 1.50 | 1.50 | 1.50 | 1.50 |
| Polyarylic acid ("PAA", Carbopol ETD 2020 Polymer) | 0.40 | 0.40 | 0.40 | 0.40 | 0.40 | — |
| Xanthan Gum ("xanth", Keltrol F) | 0.80 | 0.80 | 0.80 | 0.80 | 0.80 | 0.80 |
| Carrageenan ("carra", Genuvisco TPH-1) | 0.20 | 0.20 | 0.20 | 0.20 | 0.20 | 0.40 |
| Saccharin Sodium | 0.30 | 0.30 | 0.30 | 0.30 | 0.30 | 0.30 |
| Sodium Fluoride | 0.315 | 0.315 | 0.315 | 0.315 | 0.315 | 0.315 |
| Sodium Hydroxide | 0.06 | 0.06 | 0.06 | 0.06 | 0.06 | — |
| Titanium Dioxide | 0.70 | 0.70 | 0.70 | 0.70 | 0.70 | 0.70 |
| Flavour | 1.00 | 1.00 | 1.00 | 1.00 | 1.00 | 1.00 |
| Purified Water | ad 100 | ad 100 | ad 100 | ad 100 | ad 100 | ad 100 |
| pH (1:3 dilution in deionised water) | 5.5* | 6.0 | 6.5* | 7.0* | 7.5* | 7.0 |

*pH adjusted using NaOH or HCl

Examples 1, 2 and 3 above describe a dentifrice composition of the present invention comprising a fluoride source, a pH between 5.5 and 6.5, and the thickening agents xanthan gum, polyacrylic acid, carrageenan gum and a thickening silica. Comparative Examples A to C fall outside the scope of the present invention either having no polyacrylic acid and/or a pH greater than 5.0.

Example 4

Enamel Fluoride Uptake (EFU)

The purpose of this in vitro study was to determine the effect of various solutions containing xanthan gum and/or PAA at pH 6.0 on promoting fluoride uptake into incipient enamel lesions. The solution formulation details were as follows:

TABLE 2

| Raw Material | Solution Composition | | | |
| --- | --- | --- | --- | --- |
| | Ex D % w/v | Ex E % w/v | Ex F % w/v | Ex G % w/v |
| Sodium Fluoride | 0.061 | 0.061 | 0.061 | 0.061 |
| Xanthan Gum ("xanth", Keltrol F) | — | 0.20 | — | 0.20 |
| Polyarylic acid ("PAA", Carbopol ETD 2020 Polymer) | — | — | 0.10 | 0.10 |
| Deionised Water | ad 100 | ad 100 | ad 100 | ad 100 |
| pH (adjusted using NaOH or HCl) | 6.0 | 6.0 | 6.0 | 6.0 |

The test procedure was identical to the one identified as Procedure 40 in the FDA Monograph except the lesion was formed using a solution that was 0.1M lactic acid and 0.2% Carbopol 907 and was 50% saturated with HAP at a pH of 5.0.

Procedure

Sound, upper, central, bovine incisors were selected and cleaned of all adhering soft tissue. A core of enamel 3 mm in diameter was prepared from each tooth by cutting perpendicular to the labial surface with a hollow-core diamond drill bit. This was performed under water to prevent overheating of the specimens. Each specimen was embedded in the end of a plexiglass rod (¼" diameter×2" long) using methylmethacrylate. The excess acrylic was cut away exposing the enamel surface. The enamel specimens were polished with 600 grit wet/dry paper and then with microfine Gamma Alumina. The resulting specimen was a 3 mm disk of enamel with all but the exposed surface covered with acrylic.

Each enamel specimen was then etched by immersion into 0.5 ml of 1M HCl04 for 15 seconds. Throughout the etch period the etch solutions were continuously agitated.

A sample of each solution was then buffered with total ionic strength adjustment buffer (TISAB) to a pH of 5.2 (0.25 ml sample, 0.5 ml TISAB and 0.25 ml 1N NaOH) and the fluoride content determined by comparison to a similarly prepared standard curve (1 ml std and 1 ml TISAB). For use in depth of etch calculation, the Ca content of the etch solution was determined by taking 50 µl and analyzing for Ca by atomic absorption (0.05 ml qs to 5 ml). These data were the indigenous fluoride level of each specimen prior to treatment.

The specimens were once again ground and polished as described above. An incipient lesion was formed in each enamel specimen by immersion into a 0.1M lactic acid/0.2% Carbopol 907 solution for 24 hours at room temperature. These specimens were then rinsed well with distilled water and stored in a humid environment until used.

The treatments were performed using the mouth rinses undiluted. The specimens were immersed into 25 ml of their assigned mouth rinse with constant stirring (350 rpm) for 30 minutes. Following treatment, the specimens were rinsed with distilled water. One layer of enamel was then removed from each specimen and analyzed for fluoride and calcium as outlined above (i.e., 15 second etch). The pretreatment fluoride (indigenous) level of each specimen was then subtracted from the post treatment value to determine the change in enamel fluoride due to the test treatment.

Statistical Analyses

Statistical analyses were performed with a one-way analysis of variance model using Sigma Stat software (3.1).

Results

The results are shown in Table 3 and FIG. 1.

TABLE 3

|      | Formulation | EFU [ppm] | SEM [ppm] |
|------|-------------|-----------|-----------|
| Ex D | —           | 1230      | 34        |
| Ex E | xanth       | 1407      | 46        |
| Ex F | PAA         | 1908      | 34        |
| Ex G | xanth/PAA   | 1655      | 43        |

Treatment with Examples E, F, and G did result in a statistically significantly higher EFU than Example D, with Example F resulting in the highest EFU for all treatments. Furthermore, Example F was superior in EFU to Example E and G, with Example G being superior to Example E.

Referring to FIG. 1 it is evident the combination of xanthan gum and a polyacrylic acid (Example G) does not result in enhanced fluoride efficacy as measured by EFU when compared with a corresponding product containing a polyacrylic acid in the absence of xanthan gum (Example F). It appears that the presence of xanthan gum reduces the enhanced efficacy of oral care products containing a polyacrylic acid.

Example 5

Enamel Fluoride Uptake (EFU)

The purpose of this in vitro study was to determine the effect of the present invention on promoting fluoride uptake into incipient enamel lesions as a function of pH. The dentifrice formulations can be found in Table 1 above:

The test procedure was identical to the one identified as Procedure 40 in the FDA Monograph except the lesion is formed using a solution that was 0.1M lactic acid and 0.2% Carbopol 907 and was 50% saturated with HAP at a pH of 5.0.

Procedure

Sound, upper, central, bovine incisors were selected and cleaned of all adhering soft tissue. A core of enamel 3 mm in diameter was prepared from each tooth by cutting perpendicular to the labial surface with a hollow-core diamond drill bit. This was performed under water to prevent overheating of the specimens. Each specimen was embedded in the end of a plexiglass rod (¼" diameter×2" long) using methylmethacrylate. The excess acrylic was cut away exposing the enamel surface. The enamel specimens were polished with 600 grit wet/dry paper and then with microfine Gamma Alumina. The resulting specimen was a 3 mm disk of enamel with all but the exposed surface covered with acrylic.

Each enamel specimen was then etched by immersion into 0.5 ml of 1M HCl04 for 15 seconds. Throughout the etch period the etch solutions were continuously agitated.

A sample of each solution was then buffered with total ionic strength adjustment buffer (TISAB) to a pH of 5.2 (0.25 ml sample, 0.5 ml TISAB and 0.25 ml 1N NaOH) and the fluoride content determined by comparison to a similarly prepared standard curve (1 ml std and 1 ml TISAB). For use in depth of etch calculation, the Ca content of the etch solution was determined by taking 50 µl and analyzing for Ca by atomic absorption (0.05 ml qs to 5 ml). These data were the indigenous fluoride level of each specimen prior to treatment.

The specimens were once again ground and polished as described above. An incipient lesion was formed in each enamel specimen by immersion into a 0.1M lactic acid/0.2% Carbopol 907 solution for 24 hours at room temperature. These specimens were then rinsed well with distilled water and stored in a humid environment until used.

The treatments were performed using supernatants of the dentifrice slurries. The slurries consisted of 1 part dentifrice and 3 parts (9 g:27 ml, w/w) distilled water. The slurries were mixed well and then centrifuged for 10 minutes at ~10,000 rpm. The specimens were then immersed into 25 ml of their assigned supernatant with constant stirring (350 rpm) for 30 minutes. Following treatment, the specimens were rinsed with distilled water. One layer of enamel was then removed from each specimen and analyzed for fluoride and calcium as outlined above (i.e. 15 second etch). The pretreatment fluoride (indigenous) level of each specimen was then subtracted from the post treatment value to determine the change in enamel fluoride due to the test treatment.

Statistical Analyses

Statistical analyses were performed with a one-way analysis of variance model using Sigma Stat software (3.1).

Results

The results are shown in Table 4 and FIG. 1 below.

TABLE 4

| | Formulation | EFU [ppm] | SEM [ppm] |
|---|---|---|---|
| Ex 1 | xanth/PAA/carra, pH 5.5 | 2505 | 40 |
| Ex 2 | xanth/PAA/carra, pH 6.0 | 2121 | 51 |
| Ex 3 | xanth/PAA/carra, pH 6.5 | 1800 | 32 |
| Ex A | xanth/PAA/carra, pH 7.0 | 1722 | 57 |
| Ex B | xanth/PAA/carra, pH 7.5 | 1374 | 44 |
| Ex C | xanth/carra, pH 7.0 | 1813 | 44 |

Treatment with Examples 1 and 2 did result in a statistically significantly higher EFU than Examples 3, A, B, and C, with Example 1 resulting in the highest EFU for all treatments. There was no statistical difference in EFU between Examples 3, A, and C; however, all were superior to Example B.

Figure 2:
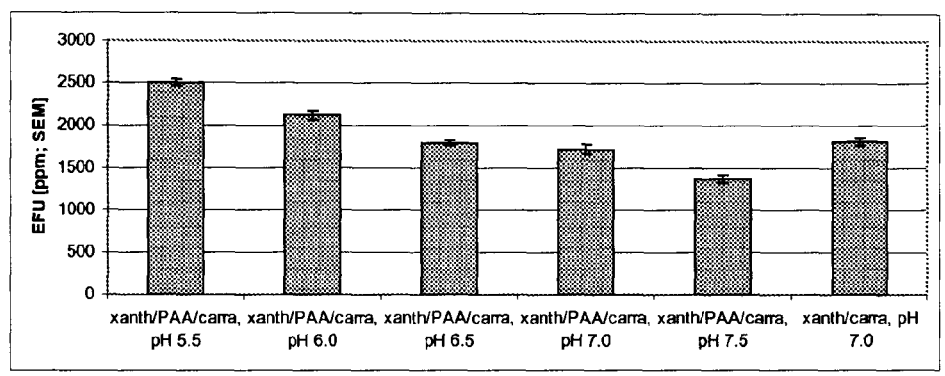
FIG. 2 depicts the strong pH dependency for EFU.

Referring to FIG. 2 it is evident that there is a strong pH dependency for EFU, and that a thickening agent system of the present invention does not lead to increased fluoride efficacy as measured by EFU at pH≥6.5 in relation to an almost identical formulation (Example C) comprising only two of the thickening agents of the present invention.

Example 6

Enamel Solubility Reduction (ESR)

The purpose of this in vitro study was to determine the effect of the present invention on the promotion of enamel resistance to lactic acid demineralization following treatments as a function of pH. The dentifrice formulations can be found in Table 1.

Procedure

Tooth Preparation

Three sound human molars were placed in a disc of red boxing wax so that only the enamel surfaces are exposed. One set of three teeth each were prepared for each dentifrice tested. All specimens were cleaned and polished with a flour of pumice slurry and a rag wheel to remove and deposits or stains.

Lactate Buffer Preparation

Two moles (203.58 g of 88.5% pure) lactic acid were diluted with approximately 500 ml of distilled water. To this was added a solution of 84 g NaOH dissolved in about 600 ml of distilled water. The total volume was then adjusted to 2000 ml. This is the buffered 1.0 M lactic acid solution.

Another 1.0 lactic acid solution was prepared by diluting two moles lactic acid to 2000 ml with distilled water. The solution of lactic acid and sodium hydroxide was placed in a 4000 ml beaker, and pH electrodes placed in the solution. The 1.0 M lactic acid solution was used to adjust the pH of the buffered solution to 4.5. To obtain a 0.1 working concentration (for all decalcifications) the 1.0 M buffer was diluted by a factor of 10 with distilled water.

Deprotection

Before every use, any residual anti-solubility protection afforded by the previous treatment is eliminated. Deprotection of these specimens will be accomplished by etching the teeth in the above prepared 0.1 M lactate buffer solution for two one-hour periods. Each disc of three specimens were agitated in about 100 ml of lactate buffer at room temperature during the two deprotection periods. The teeth were rinsed well with distilled water immediately following deprotection.

Pre-Treatment Etch

The test was performed using preheated (37° C.) tooth sets and lactate buffer in an incubator. The deprotected tooth sets were mounted on ¼ inch diameter acrylic rods with molten red boxing wax. Multiplaced stirrers were used for treatments and etches. All slurries and solutions were pre-heated to 37° C. The actual treatments and etches were done on the bench top with the preheated solutions. Plastic specimen containers (120 ml) were used for the etching procedure. A ¼ inch hole was drilled in each container lid to accommodate the plastic rod to which the tooth sets are mounted. A 40 ml portion of 0.1 M lactic acid buffer was placed in each container along with a one-inch magnetic stirring bar. The rod of the first tooth set was pushed through the hole in the lid, placed in the first container and adjusted so that all enamel surfaces were immersed into the buffer solution. The container were then placed on the first magnetic stirrer and stirring began. The timer was started at this time. At 30-second intervals the other tooth sets were started in the same manner. After 15 minutes of exposure to the buffered lactate solution, the first set was stopped and the lid and tooth set immediately removed from the container and placed in a tray of distilled water to terminate etching. The other sets were similarly removed at 30 second intervals in the same order that they were initiated and the lactate buffer solutions were retained for phosphorus analysis. The tooth sets were placed back in the 37° C. water bath in preparation for the treatment step.

Treatment

A 9-gram portion of each dentifrice was weighed and 27 ml of distilled water added to each and mixed well. The dentifrice slurries were then centrifuged for 10 minutes at 10,000 rpm. This provided enough supernatant to treat each tooth set. All tooth sets were treated at the same time (one for each product). The treatment procedure was similar to the etching procedure with the exception of the dentifrice supernatant in place of the acid. A 30 ml portion of the preheated supernatant from the dentifrice slurry was added to the first tooth set, the teeth immersed in the supernatant and the container placed on the first stirrer. The stirrer and timer was started. At 30-second intervals, the other tooth sets were started in the same manner. At the end of the five minutes of treatment, the first set was stopped, the tooth set removed and rinsed well with distilled water. The other set was removed at 30-second intervals and rinsed well. The treatment solutions will be discarded.

Post-Treatment

A second lactic acid exposure was then performed by the same method as the pre-treatment etch and the lactate buffer solutions were retained for phosphorus analysis. The pre and post-treatment solutions were analyzed using a Klett-Summerson Photoelectric Colorimeter.

Repeat Analyses

The tooth sets were deprotected and the procedure repeated additional times so that each dentifrice was treated and assayed on each tooth set. The treatment design was a Latin Square design so that no treatment followed another treatment consistently.

Calculation of E.S.R.

The percent of enamel solubility reduction was computed as the difference between the amount of phosphorus in the pre and post acidic solutions, divided by the amount of phosphorus in the pre solution and multiplied by 100.

Statistical Analysis

Statistical analyses was performed using a one-way ANOVA model with Sigma Stat software (3.1). If a significant "F" value was found, the Student Newman-Keuls (SNK) test was used to determine statistically significant differences among the individual means.

Results

Figure 3:
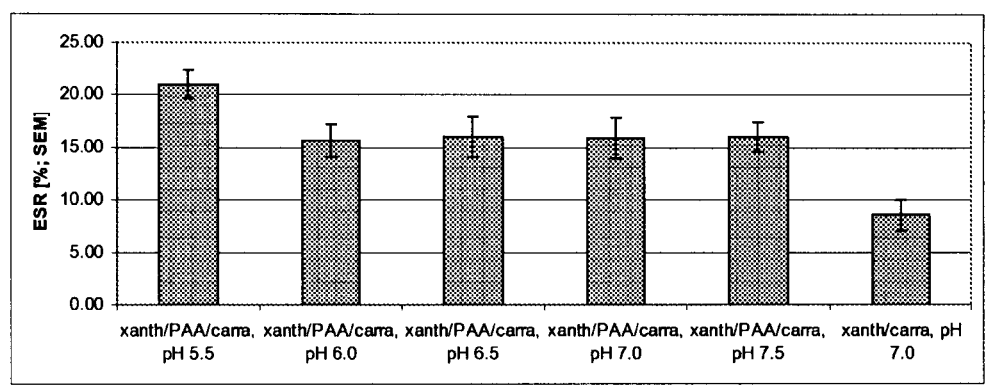
FIG. 3 depicts the results of an in vitro study conducted to determine the effect of the present invention on the promotion of enamel resistance to lactic acid demineralization following treatments as a function of pH.

The results are shown in Table 5 and FIG. 3.

TABLE 5

| | Formulation | ESR [%] | SEM [%] |
|---|---|---|---|
| Ex 1 | xanth/PAA/carra, pH 5.5 | 20.99 | 1.36 |
| Ex 2 | xanth/PAA/carra, pH 6.0 | 15.63 | 1.53 |
| Ex 3 | xanth/PAA/carra, pH 6.5 | 16.00 | 1.99 |
| Ex A | xanth/PAA/carra, pH 7.0 | 15.86 | 1.99 |
| Ex B | xanth/PAA/carra, pH 7.5 | 15.99 | 1.40 |
| Ex C | xanth/carra, pH 7.0 | 8.59 | 1.50 |

Treatment with Examples 1, 2, 3, A, and B (all containing PAA) did result in a statistically significantly higher ESR than Example C, with Example 1 resulting in the highest ESR for all treatments. There was no statistical difference in ESR between Examples 2, 3, A, and B.

Referring to FIG. 3 it is evident that there is a weak pH dependency for ESR, and that a thickening agent system of the present invention does lead to increased enamel protection as measured by ESR regardless of the pH in relation to an almost identical formulation (Example C) comprising only two of the thickening agents of the present invention.

It can be concluded from example 5 and 6 that a formulation of the present invention only leads to an increased, overall efficacy as measured by EFU and ESR at a pH≤6.5. In one embodiment the pH is 5.5 to 6.5. In another embodiment the pH is from 5.5 to 6.0.

The invention claimed is:

1. A dentifrice composition comprising a source of fluoride ions and from 0.01 to 1.5% w/w of a xanthan gum, from 0.01 to 1.5% w/w of a carbomer, from 0.01 to 2.0% w/w of a carageenan gum, a thickening silica and a silica dental abrasive and wherein the composition has a pH of between 5.5 and 6.5, provided that the composition does not contain a post-foaming agent.

2. A composition according to claim 1 wherein the pH is between 5.5 and 6.0.

3. A composition according to claim 1 wherein the polyacrylic acid is a carbomer, an acrylate/alkyl acrylate cross polymer or a polycarbophil.

4. A composition according to claim 1 wherein the carbomer is present in an amount from 0.2 to 0.6% w/w of the total composition.

5. A composition according to claim 1 wherein the xanthan gum is present in an amount from 0.5 to 1.0% w/w of the total composition.

6. A composition according to claim 1 wherein the carageenan gum is present in an amount from 0.1 to 0.3% w/w of the total composition.

7. A composition according to claim 6 additionally comprising a silica dental abrasive.

8. A composition according to claim 1 wherein the fluoride ion source is sodium fluoride.

9. A composition according to claim 1 comprising a desensitising agent.

10. A composition according to claim 1 comprising a whitening agent.

11. A composition according to claim 1 comprising an oral malodour agent.

12. A composition according to claim 1 in the form of a striped dentifrice.

* * * * *